United States Patent
Van Grinsven et al.

(10) Patent No.: US 10,324,087 B2
(45) Date of Patent: Jun. 18, 2019

(54) THERMOCOUPLES COMPRISING A POLYMER FOR DETECTING ANALYTES AND RELATED METHODS

(71) Applicants: Universiteit Maastricht, Maastricht (NL); Academisch Ziekenhuis Maastricht, Maastricht (NL)

(72) Inventors: Bart Robert Nicolaas Van Grinsven, Heerlen (NL); Thomas Jan Cleij, Elsloo (NL)

(73) Assignees: Universiteit Maastricht, Maastricht (NL); Academisch Ziekenhuis Maastricht, Maastricht (NL)

(*) Notice: Subject to any disclaimer, the term of this patent is extended or adjusted under 35 U.S.C. 154(b) by 409 days.

(21) Appl. No.: 15/095,653

(22) Filed: Apr. 11, 2016

(65) Prior Publication Data
US 2017/0292949 A1    Oct. 12, 2017

(51) Int. Cl.
*G01N 33/543* (2006.01)
*G01N 25/48* (2006.01)

(52) U.S. Cl.
CPC ..... *G01N 33/54373* (2013.01); *G01N 25/482* (2013.01); *G01N 2600/00* (2013.01)

(58) Field of Classification Search
None
See application file for complete search history.

(56) References Cited

U.S. PATENT DOCUMENTS

| | | | |
|---|---|---|---|
| 4,924,037 A | 5/1990 | Ainsworth et al. |
| 6,161,028 A | 12/2000 | Braig et al. |
| 8,932,868 B2 | 1/2015 | Van Grinsven et al. |
| 2003/0059807 A1 | 3/2003 | Roach et al. |
| 2003/0199742 A1 | 10/2003 | Braig et al. |
| 2004/0034291 A1 | 2/2004 | Braig et al. |
| 2004/0087841 A1 | 6/2004 | Braig et al. |
| 2004/0126814 A1 | 7/2004 | Singh et al. |
| 2006/0078999 A1 | 4/2006 | Bell et al. |
| 2009/0281272 A1 | 11/2009 | Yilmaz et al. |

(Continued)

FOREIGN PATENT DOCUMENTS

| CN | 101415487 A | 4/2009 |
|---|---|---|
| EP | 2772753 A1 | 9/2014 |

(Continued)

OTHER PUBLICATIONS

European Search Report of copending EP application 15 19 4837 dated Feb. 22, 2016.

(Continued)

*Primary Examiner* — Rebecca L Martinez
(74) *Attorney, Agent, or Firm* — TraskBritt (57) ABSTRACT

A device for detecting an analyte includes a thermocouple having an assay polymer over a surface of the thermocouple. The assay polymer is formulated to bind to the analyte, and a heat transfer property of the assay polymer varies responsive to an amount of the analyte bound thereto. A method of forming a sensor includes providing an assay polymer over a thermocouple. A method for detecting an analyte includes passing a liquid containing an analyte adjacent a thermocouple having an assay polymer over a surface thereof, binding an analyte to the assay polymer, detecting a temperature of the thermocouple, and calculating a concentration of the analyte in the liquid based at least in part on the heat transfer property of the assay polymer.

20 Claims, 7 Drawing Sheets

(56) References Cited

U.S. PATENT DOCUMENTS

| | | |
|---|---|---|
| 2010/0319436 A1 | 12/2010 | Sun et al. |
| 2013/0327656 A1 | 12/2013 | Van Grinsven et al. |
| 2014/0011198 A1 | 1/2014 | Van Grinsven et al. |
| 2014/0242605 A1 | 8/2014 | Eersels et al. |
| 2015/0219584 A1 | 8/2015 | Van Grinsven et al. |

FOREIGN PATENT DOCUMENTS

| | | |
|---|---|---|
| JP | 2005345385 | 12/2005 |
| WO | 0053086 | 9/2000 |
| WO | 2004079001 A1 | 9/2004 |
| WO | 2012076349 A1 | 6/2012 |

OTHER PUBLICATIONS

Van Grinsven et al., The Heat-Transfer Method: A Versatile Low-Cost, Label-Free, Fast and User-Friendly Readout Platform for Biosensor Applications, ACS Applied Materials and Interfaces, Aug. 8, 2014, pp. 13309-13318, vol. 6, No. 16.

Marloes Peeters et al: Introducing Thermal Wave Transport Analysis (TWTA) A Thermal Technique for Dopamine Detection by Screen-Printed WElectrodes Functionalized with Moleculary Imprinted Molecules, vol. 21, No. 5, Apr. 26, 2016 (Apr. 26, 2016), p. 552.

M. Peeters et al: "Heat-transfer-based detection of 1-nicotine, histamine, and serotonin as biomimetic receptors", Analytical and Bioanalytical Chemistry, vol. 405, No. 20, May 18, 2013 (May 18, 2013), pp. 6453-6460.

Kasper Eersels et al: "Selective Identification of Macrophages and Cancer Cells Based on Thermal Transport through Surface-Imprinted Polymer Layers", ACS Applied Materials and Interfaces, vol. 5, No. 15, Aug. 14, 2013 (Aug. 14, 2013), pp. 7258-7267.

International Written Opinion received for PCT Patent Application No. PCT/EP2016/076572, dated Apr. 10, 2017, 6 pages.

International Search Report received for PCT Patent Application No. PCT/EP2016/076572, dated Apr. 10, 2017, 5 pages.

Gideon Wackers et al: "Array Formatting of the Heat-Transfer Method (HTM) for the Detection of Small Organic Molecules by Molecularly Imprinted Polymers", Sensors, vol. 14, No. 6, Jun. 20, 2014 (Jun. 20, 2014), pp. 11016-11030.

THERMOCOUPLES COMPRISING A POLYMER FOR DETECTING ANALYTES AND RELATED METHODS

TECHNICAL FIELD

Embodiments of the present disclosure relate generally to devices and methods of detecting analytes using a thermocouple having a polymer material thereon.

BACKGROUND

Molecularly imprinted polymers (MIPs) can be used for detecting chemical substances in complex mixtures. In modern research, these polymers are of increasing interest for bioanalytical applications. Advantages of using these MIPs include easy and cheap production; mechanical, chemical, and thermal stability; reusability; and long shelf life. In recent years, the concept of molecular imprinting has been extended to surface imprinting of thin polymer films with micrometer sized cells to create so-called "surface imprinted polymers" (SIPs) for the detection of proteins, glycoproteins, plant viruses, human viruses, bacteria, pollen, yeast cells, and even mammalian red blood cells. SIPs are polymeric materials with indentations at the surface, with a form and function matching part of a desired target. SIPs are suitable for bonding with larger objects (e.g., cells, bacteria, etc.) which do not diffuse quickly through pores of an MIP. Imprinting may occur after polymerization by softening the polymer. The detection of cells using biosensors described in literature is typically done by gravimetric detection, electronic read-out platforms or micro-fluidic techniques. However, these techniques are often time-consuming, provide difficulties for analysis, or require expensive equipment.

For example, temperature resistance of substrates having MIPs attached thereto based on the concentration of analytes is described in U.S. Patent Application Publication 2014/0011198 A1, "Heat-Transfer Resistance Based Analysis Bioparticles," published Jan. 9, 2014, the entire disclosure of which is hereby incorporated herein by reference.

A low-cost sensor platform able to differentiate between cells with slight differences in shape, size, and functionalities in functional groups on their surface would be a valuable tool for modern research and industry.

BRIEF SUMMARY

In some embodiments, a device for detecting an analyte includes a thermocouple having an assay polymer over a surface of the thermocouple. The assay polymer is formulated to bind to the analyte, and a heat transfer property of the assay polymer varies responsive to an amount of the analyte bound thereto.

A method of forming a sensor includes providing an assay polymer over a thermocouple. The assay polymer is formulated to bind to an analyte, and the assay polymer is formulated such that a heat transfer property of the assay polymer varies responsive to an amount of the analyte bound thereto.

In certain embodiments, a method for detecting an analyte includes passing a liquid containing an analyte adjacent to and in contact with a thermocouple having an assay polymer over a surface thereof, binding an analyte to the assay polymer, detecting a temperature of the thermocouple, and calculating a concentration of an analyte in the liquid based at least in part on the heat transfer property of the assay polymer. A heat transfer property of the assay polymer is formulated to vary responsive to an amount of the analyte bound thereto.

DETAILED DESCRIPTION

The illustrations presented herein are not actual views of any particular device or method, but are merely idealized representations employed to describe example embodiments of the present disclosure. Elements common between figures may retain the same numerical designation.

As used herein, the term "template molecule" refers to a molecule used to form a molecularly imprinted polymer (MIP) or surface imprinted polymer (SIP). Such MIPs or SIPs can then detect "target molecules" or "binding partners," which have a geometry at least partially corresponding to the template molecules used to form the MIP or SIP.

As used herein, the term "may" encompasses the word "can," and the term "may be" encompasses the words "is" or "are," depending on context. Furthermore, presence of the word "may" is intended to explain options for practicing or implementing the disclosure, without limitation.

Figure 1:
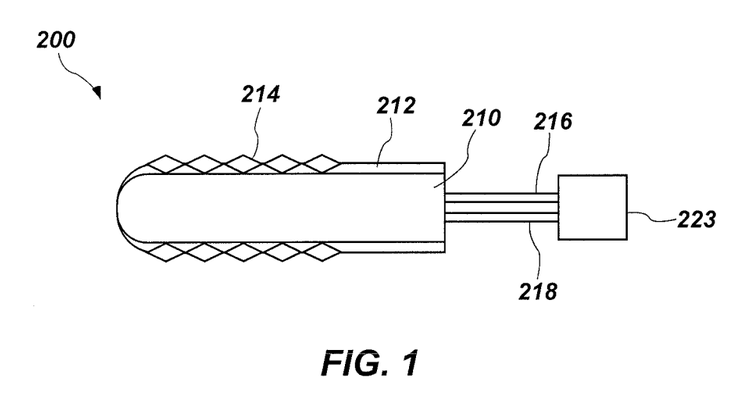
FIG. 1 is a simplified schematic diagram showing a device for detecting an analyte.

FIG. 1 is a simplified schematic diagram showing a device 200 for detecting an analyte. In some embodiments, the device 200 may be configured to detect a target molecule, a nucleic acid such as DNA and/or RNA, single-nucleotide polymorphisms (SNPs) in DNA and/or RNA, small molecules, proteins, etc.

The device 200 may include a thermocouple 210 having a base material 212 formed over a surface thereof. For example, the base material 212 may be formed over a generally cylindrical surface of the thermocouple 210, such that an entire end of the thermocouple 210 is enclosed. In some embodiments, the exterior surface of the thermocouple 210 may have any appropriate cross-sectional shape, such as a circle, square, rectangle, etc. That is, the thermocouple 210 need not be cylindrical, but may have a "ribbon" shape, etc. The thermocouple 210 may include a junction between two materials formulated to provide a temperature-dependent voltage between electrical contacts 216, 218. In some embodiments, the thermocouple 210 may include one or more of a metal (e.g., platinum, gold, iridium, palladium, etc.) or an alloy (e.g., a nickel alloy, a copper alloy, a rhodium alloy, a rhenium alloy, an iron alloy, a molybdenum alloy, etc.). The thermocouple 210 may be, for example, any commercially available standard thermocouple, such as a Type E thermocouple (i.e., chromel and constantan); a Type J thermocouple (i.e., iron and constantan); a Type K thermocouple (i.e., chromel and aluminum); a Type M thermocouple (i.e., nicrosil and nisil); a Type T thermocouple (i.e., copper and constantan); a Type B, R, or S thermocouple (i.e., platinum-rhodium alloys); a Type C, D, or G thermocouple (i.e., tungsten-rhenium alloys); a Type P thermocouple (i.e., palladium-gold-platinum alloys); etc.

The base material 212 may be a polymer material such as polylactic-(L)-acid, which may be referred to in the art as PLLA. PLLA is transparent, inexpensive to produce from environmentally renewable sources (e.g., starch or sugar-containing agricultural products), biodegradable, and biocompatible. Furthermore, PLLA can be solubilized in chloroform to enable application to the thermocouple 210. The base material 212 may be selected to be another material instead of PLLA, based on desired properties. In some embodiments, the base material 212 may include polyurethane, polylactic acid, polycaprolactone, poly(lactic-co-glycolic acid), poly(D,L-lactide-co-glycolide), or another selected polymer. The base material 212 may be in the form of a thin, smooth, and homogeneous coating over the exterior of the thermocouple 210. Uniformity of the base material 212 may enable to the device 200 to yield reproducible results. The thickness of the base material 212 may vary proportionally with the thermal resistance of the 212 to heat flow toward or away from the thermocouple 210. Thus, a thinner base material 212 may be beneficial for applications in which a fast response is desired or temperature differentials are small.

The base material 212 may be selected to be elastic, such that the device 200 may be flexible to allow bending of the thermocouple 210 without breaking the base material 212. This may enable the device 200 to be used for applications requiring tight clearance or bends (e.g., in vivo use in catheters).

An assay polymer 214 may be on a surface of the base material 212. In some embodiments, the assay polymer 214 may be directly bonded to the surface of the thermocouple 210, and the base material 212 may be omitted. The assay polymer 214 may include a material for which a heat transfer property varies responsive to an amount of the analyte bound thereto. For example, the thermal conductivity, thermal diffusivity, heat capacity, or another property of the assay polymer 214 may vary with concentration of the analyte on the surface thereof.

In some embodiments, the assay polymer 214 may include an imprinted polymer, such as a molecularly imprinted polymer (MIP) or surface imprinted polymer (SIP). MIPs and SIPs may also be referred to in the art as "plastic" antibodies. MIPs typically possess a high affinity for a specific binding partner, so that when such binding partners are contacted with the MIP, the molecules bind with the MIP. MIPs are synthetic receptors that contain nanocavities with high affinity for their respective target molecules. Imprinting (i.e., formation of the nanocavities) is often part of the polymerization process. MIPs are able to specifically bind targets varying from small ions to large cells in complex matrices. Binding of the molecules to the MIP may alter some properties of the MIP, such as thermal properties, mechanical properties, electrical properties, etc. MIPs may therefore be used to detect such molecules at relatively low concentrations. MIPs are described in, for example, U.S. Patent Application Publication 2009/0281272 A1, "Monodisperse Molecularly Imprinted Polymer Beads," published Nov. 12, 2009, the entire disclosure of which is hereby incorporated herein by reference.

Similarly, SIPs typically possess a high affinity for a specific binding partner, but may typically bind to relatively larger objects (e.g., cells, bacteria, etc.) that do not diffuse quickly through pores of an MIP. SIPs may be polymer materials formed over a surface, then imprinted after polymerization by softening the polymer.

When the device 200 is in contact with a liquid carrying the analyte, a portion of the analyte may bind to the assay polymer 214, changing the heat transfer property thereof.

In certain embodiments, the assay polymer 214 may include DNA, RNA, proteins, or portions or analogs thereof (e.g., antibodies). For example, the device 200 may include a base material 212 (e.g., a diamond surface) functionalized with a assay polymer 214 such as DNA, RNA, a protein, a polypeptide, a nucleic acid polymer, a probe, or a portion or analog thereof (e.g., complementary DNA). The assay polymer 214 may be configured to possess a high affinity for a specific binding partner, so that when such binding partners are contacted with the surface of the thermocouple 210, the molecules bind with the assay polymer 214. In some embodiments, the assay polymer 214 may include at least about seven (7) repeating units, such as ten (10) repeating units or more.

In some embodiments, the device 200 may include a processor 223 programmed to calculate an amount of the analyte bound to the assay polymer 214. The processor 223 may calculate a concentration of the analyte in a liquid in contact with the device 200 based at least in part on the amount of the analyte bound to the assay polymer 214. For example, the processor 223 may calculate the amount of the analyte by a method as disclosed in U.S. Patent Application Publication 2014/0011198 A1, "Heat-Transfer Resistance Based Analysis Bioparticles," published Jan. 9, 2014; or U.S. Patent Application Publication 2014/0242605 A1, "Heat-Transfer Resistance Based Analysis of Bioparticles," published Aug. 28, 2014, the entire disclosures of each of which are hereby incorporated herein by reference. In certain embodiments, the processor 223 may be used to detect a phase shift between a thermal wave at or emanating from a heat sink and an attenuated thermal wave at the thermocouple 210. The processor 223 may then calculate the concentration of the analyte in the liquid based at least in part on a difference in amplitude between the thermal wave at the heat sink and the attenuated thermal wave at the thermocouple 210.

Figure 2A:
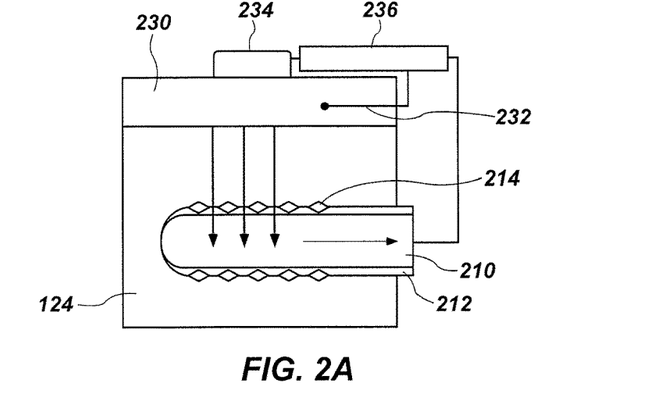
FIG. 2A through 2C are simplified schematic diagrams showing how the device of FIG. 1 may be used to detect an analyte.
Figure 2B:
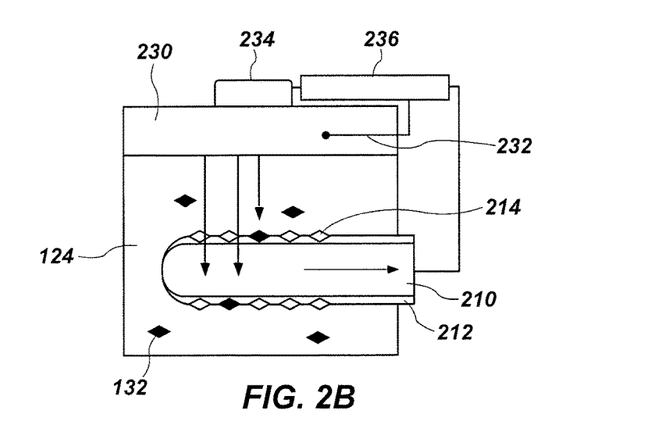
Figure 2C:
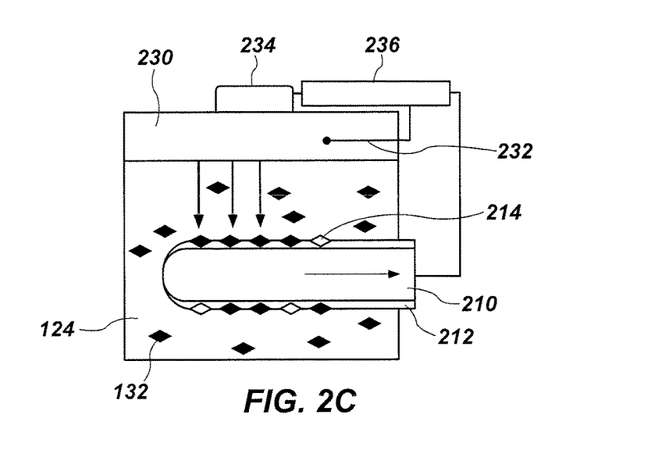

FIGS. 2A through 2C illustrate how the device 200 shown in FIG. 1 may be used to detect an analyte 132 in a liquid 124. The liquid 124 may be passed adjacent to the thermocouple 210. The liquid 124 may include an analyte 132 that specifically binds to the assay polymer 214 and changes thermal properties thereof, as described above. A heat sink 230 may provide heat to the liquid 124. Though referred to as a heat "sink" for the sake of simplicity, the heat sink 230 may be configured to provide heat to or remove heat from the liquid 124 and, so, may also be characterized as a heat transfer element 230. The heat sink or heat transfer element 230 may be a material having a high thermal conductivity, such as a transition metal (e.g., copper, silver, etc.) or an alloy or mixture thereof. The heat sink 230 may be thermally coupled to a temperature sensor 232 (e.g., a thermocouple or another device) configured to detect a temperature of the heat sink 230, and to a temperature modification device 234 configured to maintain the temperature of the heat sink 230.

If the properties of the heat sink 230 are known (e.g., if a relationship between a control signal to the modification device 234 and the temperature of the heat sink 230 is well characterized), the temperature sensor 232 may be omitted. In some embodiments, the temperature sensor 232 may be integral to the temperature modification device 234. For example, the resistance of the temperature modification device 234 itself may be measured to determine its temperature. The temperature modification device 234 may include, for example, a thermoelectric device, a heat exchanger, a fan, a resistance heater, etc. The temperature sensor 232 may be a resistor having a resistance that varies with temperature. The temperature of the liquid 124 may be different from the temperature of the heat sink 230, and may vary based at least in part on the presence or absence of the analyte 132 and its concentration in the liquid 124.

The temperature sensor 232 and the temperature modification device 234 may be connected to a processor 236 programmed to control the temperature modification device 234 to cause the heat sink 230 to produce a thermal wave emanating from the heat sink 230 and through the liquid 124 to the thermocouple 210. For example, the processor 236 may be a computer having an input-output card configured to receive and provide electrical signals, or any other suitable controller. The processor 236 may be a proportional-integral-derivative (PID) controller capable of changing the temperature of the heat sink 230 by a small amount on a relatively short time scale. For example, the processor 236 may be programmed to change the temperature of the heat sink 230 by about 0.5° C. or less, about 0.2° C. or less, or even about 0.05° C. or less. Thus, the thermal wave may have an amplitude of about 1.0° C. or less, about 0.4° C. or less, or even about 0.10° C. or less. The processor 236 may be capable of changing the temperature of the heat sink 230 via the temperature modification device 234 from one set point to another and back to form a thermal wave having a frequency from about 0.001 to about 0.5 Hz, such as from about 0.005 to about 0.1 Hz, or from about 0.01 to about 0.05 Hz. In some embodiments, the processor 236, the temperature modification device 234, and the heat sink 230 may together produce a thermal wave having a variable frequency. Based on a measurement from the temperature sensor 232 (if present), a known input to the temperature modification device 234, or other means, properties of the thermal wave may be known (e.g., a phase, amplitude, frequency at a specific time, rate of frequency change, etc.).

As shown in FIG. 2A, the liquid 124 may be substantially free of the analyte 132 of interest at one point in time, and the assay polymer 214 may also be substantially free of the analyte 132 at that time. Thus, heat (indicated by arrows in FIG. 2A) may be transferred from the heat sink 230 through the liquid 124 to the thermocouple 210 and along the thermocouple 210 at a rate related to the heat transfer properties of the assay polymer 214 unbound with the analyte 132 (because the thermocouple 210 itself may provide minimal thermal resistance).

At another time, shown in FIG. 2B, the liquid 124 may have a nonzero concentration of the analyte 132, and some of the analyte 132 may bind to the assay polymer 214. Therefore, heat may be transferred from the heat sink 230 through the liquid 124 to the thermocouple 210 at a different rate than shown in FIG. 2A (as indicated by the arrows in FIG. 2B). At yet another time, shown in FIG. 2C, the liquid 124 may have a higher concentration of the analyte 132 than shown in FIG. 2B, and more of the analyte 132 may bind to the assay polymer 214. Therefore, heat may be transferred from the heat sink 230 through the liquid 124 to the thermocouple 210 at a different rate than shown in FIGS. 2A and 2B. For example, an increase in the amount of the analyte 132 bound to the assay polymer 214 may decrease the heat transfer rate through the assay polymer 214 to the thermocouple 210.

The concentration of the analyte 132 in the liquid 124 may be calculated based at least in part on a heat transfer property of the assay polymer 214 (which may be inferred based on, e.g., the amount of heat transferred to the thermocouple 210 as a function of time).

Figure 3A:
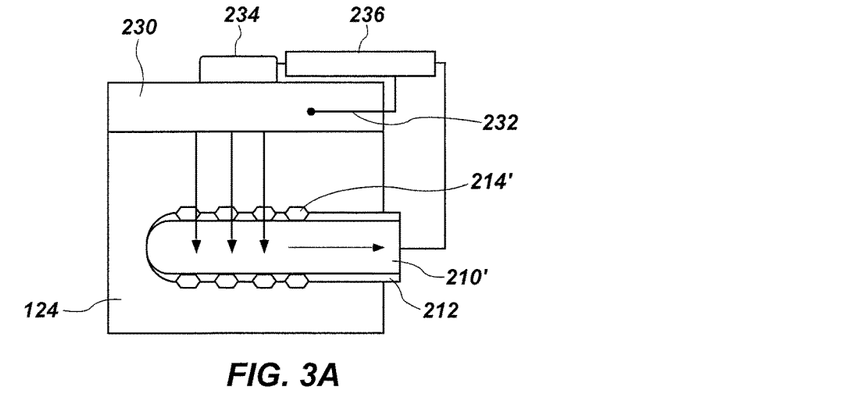
FIGS. 3A through 3C are simplified schematic diagrams comparatively showing how other devices would react when exposed to an analyte under the conditions shown in FIGS. 2A through 2C.
Figure 3B:
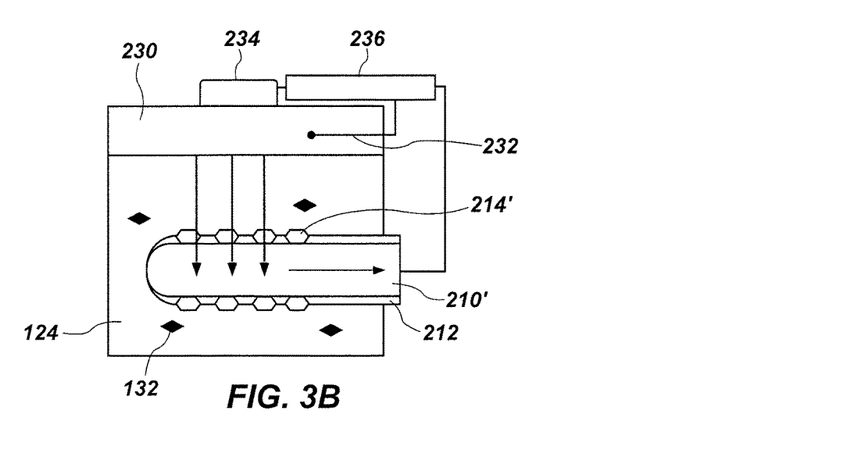
Figure 3C:
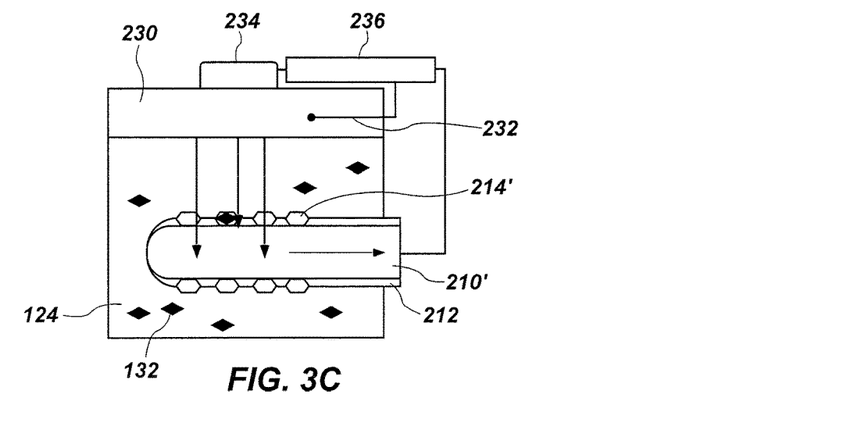

For comparison purposes, FIGS. 3A through 3C illustrate how a thermocouple 210' having a polymer 214' that does not have an affinity for the analyte 132 (e.g., a non-imprinted polymer) may perform under similar conditions to those shown in FIGS. 2A through 2C. In FIG. 3A, the liquid 124 may be substantially free of the analyte 132 of interest at one point in time, and the polymer 214' may also be substantially free of the analyte 132 at that time. At another time, shown in FIG. 3B, the liquid 124 may have a nonzero concentration of the analyte 132, yet the analyte 132 may not bind to the polymer 214' in an appreciable amount. Therefore, heat (indicated by arrows in FIG. 3A) may be transferred from the heat sink 230 through the liquid 124 to the thermocouple 210 at the same rate shown in FIG. 3A. At yet another time, shown in FIG. 3C, the liquid 124 may have a higher concentration of the analyte 132 than shown in FIG. 3B, yet the analyte 132 may still not bind to the polymer 214' to an appreciable amount. Some portion of the analyte 132 may bind to the polymer 214', particularly for high concentrations of the analyte 132 in the liquid 124, but the amount of analyte 132 bound may be much smaller than the amount bound to the assay polymer 214 (FIG. 2C) at similar concentrations. Heat may be transferred from the heat sink 230 through the liquid 124 to the thermocouple 210' at substantially similar rates no matter the concentration of the analyte 132 in the liquid 124.

Referring again to FIGS. 2A through 2C, a processor 236 (which may be or include the processor 223 shown in FIG. 1, or which may be in electronic communication with the processor 223) may be programmed to calculate a concentration of the analyte 132 in the liquid 124 based at least in part on a thermal wave emanating through the liquid 124. For example, the heat sink 230 may cause a change in a temperature of the liquid 124, and may form a thermal wave through the liquid 124. The processor 236 may determine a difference in amplitude and/or phase between the thermal wave as provided by the heat sink 230 and an attenuated thermal wave at the thermocouple 210. The difference in amplitude and/or phase may be used to determine the amount of the analyte 132 bound to the assay polymer 214, which may in turn be used to determine the concentration of the analyte 132 in the liquid 124.

In some embodiments, the processor 236 may implement a frequency change of the thermal wave produced by the heat sink 230. The processor 236 may then detect a phase shift between the thermal wave produced by the heat sink 230 and an attenuated thermal wave in the liquid 124 after the thermal wave passes through the assay polymer 214 and the base material 212 to the thermocouple 210.

Figure 4:
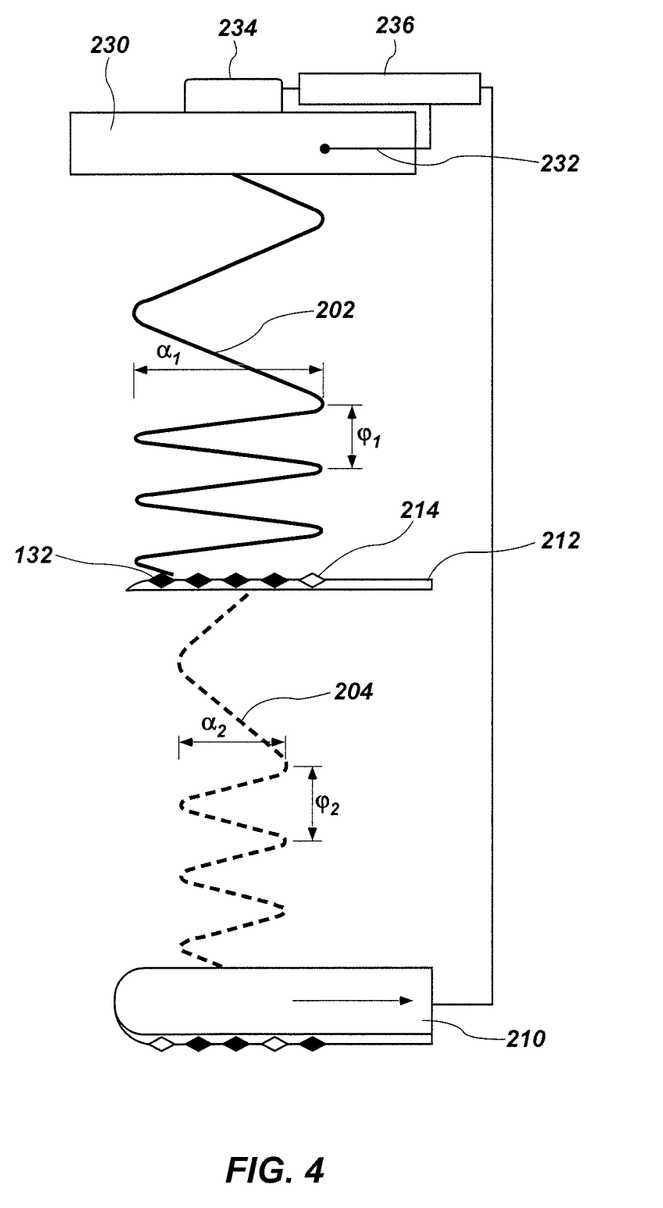
FIG. 4 is a simplified expanded view showing how a thermal wave may travel in the device of FIG. 1 through 2C.

FIG. 4 is a simplified schematic representation showing how the thermal wave may travel into and within the device 200 of FIG. 1. FIG. 4 includes some of the components shown in FIGS. 1 and 2A through 2C, but shows them separated to allow representation of thermal waves traveling through and between the components. In particular, FIG. 4 shows the heat sink 230 thermally coupled to the temperature modification device 234 and the temperature sensor 232, which are connected to the processor 236.

The heat sink 230 may produce a thermal wave 202 and transfer the thermal wave 202 to the liquid 124 toward the assay polymer 214 on the thermocouple 210. For example, if the heat sink 230 is initially maintained at a constant temperature of 37° C., the thermal wave 202 may be produced by heating the heat sink 230 to a temperature of 37.1° C. and then cooling the heat sink 230 to a temperature of 36.9° C. The heating and cooling of the heat sink 230, driven by the temperature modification device 234, may cause the assay polymer 214 and the thermocouple 210 to heat and cool in a corresponding manner. The thermal wave 202 may have an amplitude $\alpha_1$ and a frequency $\varphi_1$. The amplitude $\alpha_1$ and/or the frequency $\varphi_1$ may vary with time. For example, the thermal wave 202 may have a continuously varying frequency $\varphi_1$.

As discussed above, the presence or absence of the analyte 132 on the assay polymer 214 may change the thermal conductivity, thermal diffusivity, heat capacity, or another property of the assay polymer 214. The assay polymer 214 may define cavities therein adapted to interact with at least a portion of the analyte 132. Without being bound to any particular theory, the cavities may be configured to act to specifically bind the analyte 132. Thus, the assay polymer 214 may receive particles or molecules of the analyte 132 from the liquid 124 in some of the cavities, based on the concentration of the analyte 132 in the liquid 124. The liquid 124 and the assay polymer 214 may reach equilibrium at a given temperature, such that the analyte 132 binds to and separates from the assay polymer 214 at equal rates. The thermal properties of the assay polymer 214 may depend in part on the fraction of the cavities bound to particles or molecules of the analyte 132.

The assay polymer 214 and/or the analyte 132 thereon may alter the thermal wave 202 passing therethrough to form an attenuated thermal wave 204. The attenuated thermal wave 204 may be detected by the thermocouple 210, and recorded by the processor 236. The attenuated thermal wave 204 may have an amplitude $\alpha_2$ and a frequency $\varphi_2$, which may be different from the amplitude $\alpha_1$ and a frequency $\varphi_1$ of the thermal wave 202. The differences in the amplitudes $\alpha_1$, $\alpha_2$ and/or the frequencies $\varphi_1$, $\varphi_2$ may be correlated to the amount of the analyte 132 bound to the assay polymer 214, and thus, to the concentration of the analyte 132 in the liquid 124. Measurement of the differences in the amplitudes $\alpha_1$, $\alpha_2$ and/or the frequencies $\varphi_1$, $\varphi_2$ may allow the device 200 to detect relatively lower amounts of the analyte 132 bound to the assay polymer 214 (corresponding to lower concentrations of the analyte 132 in the liquid 124) as compared with methods of measuring the temperature of the thermocouple 210 at steady state.

Referring again to FIG. 1, to form the device 200, the base material 212 may be formed or otherwise provided over the thermocouple 210. For example, the thermocouple 210 may be dip-coated with the base material 212 by immersing a portion of the thermocouple 210 into a liquid containing the base material 212 or a precursor thereof. Dip-coating may be performed efficiently and scaled to produce mass quantities, with relatively high uniformity in comparison with other methods. Dip-coating of wire is described in, for example, U.S. Pat. No. 4,924,037, "Electrical Cable," granted May 8, 1990, the entire disclosure of which is hereby incorporated herein by reference. Dip-coating may form the base material 212 to be relatively thin, such that the base material 212 has a relatively low intrinsic thermal resistivity than thicker layers of polymer. For example, the base material 212 may have a thickness from about 0.01 mm to about 1 mm, such as from about 0.05 mm to about 0.5 mm.

The assay polymer 214 may be provided over and secured to the base material 212. In some embodiments, the thermocouple 210 with the base material 212 thereon may be heated such that the base material 212 softens. For example, the base material 212 may be heated to a temperature above its glass transition temperature ($T_g$). The thermocouple 210 and base material 212 coating may then be rolled in a powder of the assay polymer 214 to attach the assay polymer 214 to the base material 212. The base material 212 may then be cooled to retain the particles of the assay polymer 214, such as by cooling the base material 212 to a temperature below $T_g$. The time between attaching particles of the assay polymer 214 and cooling the base material 212 may be kept relatively short, such that the particles of the assay polymer 214 can become securely embedded into the base material 212 without becoming covered by the polymer 212. For example, the thermocouple 210 may be placed in a refrigerator to cool the base material 212 within about a time period from about 1 second to about 60 seconds after coating with the assay polymer 214. The thermocouple 210 may remain in the refrigerator until the base material 212 is in a solid phase (e.g., crystalline). For example, the thermocouple 210 may remain in the refrigerator for a time period from about 1 minute to about 20 minutes. After cooling, the thermocouple 210 may be washed in a liquid (e.g., water, alcohol, etc.) to remove loosely bound or unbound particles of the assay polymer 214 from the surface of the base material 212.

Without being bound to any particular theory, it appears that above Tg, polymers soften and plasticize, meaning that the time the thermocouple 210 spends above Tg may allow particles of the assay polymer 214 to sink into or otherwise bond to the base material 212.

The processor 236 (e.g., a PID controller) may be electrically connected to the temperature modification device 234 to provide power sufficient to drive the temperature of the heat sink 230, and to cause the temperature modification device 234 to change the temperature of the heat sink 230 to produce the thermal wave 202 (FIG. 4).

The thermocouple 210 may be disposed within a flow of the liquid 124 to be measured. The heat sink 230 may be secured to a conduit through which the liquid 124 passes, or may be disposed within the flow of the liquid 124. The processor 236 may be configured to continuously detect the temperature at the thermocouple 210 and the temperature sensor 232, and to calculate the concentration of the analyte 132 in the liquid 124 based at least in part on a phase shift between the thermal wave 202 (FIG. 4) produced by the heat sink 230 and the attenuated thermal wave 204 (FIG. 4) at the thermocouple 210.

The device 200 shown and described may be configured to detect any of a wide range of selected analytes 132. For example, the device 200 may be used for detecting, sensing, or quantifying biological analytes or other chemicals in the liquid 124. The analyte 132 may be a gas, liquid, or solid dissolved or otherwise mixed with the liquid 124. For example, the device 200 may be used for detecting, sensing, quantifying analytes, antibodies, antigens, nucleic acids, (e.g., DNA, RNA, etc.), including nucleic acids with particular sequences (e.g., SNPs), proteins, small molecules (e.g., dopamine, histamine, etc.) or other substances. In some embodiments, the device 200 may be used for detecting histamine, dopamine, serotonin, adrenalin, methylphenidate, etc.

One of the many attractive features of molecular imprinting methods as disclosed herein is that methods can be applied to a diverse range of analytes. The imprinting of small, organic molecules (e.g., pharmaceuticals, pesticides, amino acids and peptides, nucleotide bases, steroids, sugars, etc.) is described in, for example, K. Haupt and K. Mosbach, "Molecularly Imprinted Polymers and Their Use in Biomimetic Sensors," Chem. Rev. 100, 2495-2504 (2000); and G. Mustafa and P. Lieberzeit, "MIP Sensors on the Way to Real-World Applications," in Springer Series on Chemical Sensors and Biosensors, vol. 12, pp. 167-187 (Springer, 2012). Somewhat larger organic compounds (e.g., peptides) can also be imprinted via similar approaches. Protocols for imprinting larger structures, such as proteins, cells, and mineral crystals have been proposed in, for example, M. Kempe, M. Glad, and K. Mosbach, "An Approach Towards Surface Imprinting Using the Enzyme Ribonuclease A," J. Molecular Recognition, 8, 35-39 (1995); S. Hjerten et al., "Gels Mimicking Antibodies in Their Selective Recognition of Proteins," Chromatographia 44, 227-234 (1997); H. Shi et al., "Template-Imprinted Nanostructured Surfaces for Protein Recognition," Nature 398, 593-597 (1999); A. Aherne et al. "Bacteria-Mediated Lithography of Polymer Surfaces," J. Am. Chem. Soc. 118, 8771-8772 (1996); and S. M. D'Souza, et al., "Directed Nucleation of Calcite at a Crystal-Imprinted Polymer Surface," Nature 398, 312-316 (1999). Molecular imprinting as a bridge to drug advanced drug delivery is described in B. Sellergren and C. Allender, "Molecularly Imprinted Polymers: A Bridge to Advanced Drug Delivery," Advanced Drug Delivery Reviews 57, 1733-1741 (2005). The entire disclosures of each of the documents cited in this paragraph are hereby incorporated herein by reference.

To detect the analyte 132, the liquid 124 containing the analyte 132 may be passed through a conduit adjacent the assay polymer 214 over the thermocouple 210. Particles or molecules of the analyte 132 bind to the assay polymer 214, changing one or more thermal properties of the assay polymer 214. The liquid 124 may flow continuously adjacent the assay polymer 214 during detection, or the flow may terminate before detection begins. The thermal wave 202 (FIG. 4) and the attenuated thermal wave 204 may travel through the liquid 124 whether the liquid 124 is flowing or stagnant. The thermal properties of liquid 124 may differ for flowing and stagnant liquids 124, but can be determined based on flow properties. In some embodiments, the liquid 124 may be brought to a test temperature before detection of the analyte 132. As discussed above, the assay polymer 214 may be a molecularly imprinted polymer formulated to bind a particular analyte 132 of interest.

The thermal wave 202 (FIG. 4) is provided from the adjustable heat sink 230 to the thermocouple 210 through the assay polymer 214. The processor 236 (e.g., a PID controller) may change the temperature of the heat sink 230 via the temperature modification device 234, such as by raising the temperature and lowering the temperature of the heat sink 230 by a preselected amount and at a preselected frequency. The change in the temperature of the heat sink 230 may be small enough that the change does not interfere significantly with other measurements that may occur simultaneously. For example, the average temperature of the liquid 124 may be measured even though the temperature of the heat sink 230 is varying, so long as the time scale of the average temperature measurement is longer than the frequency of the variation and/or the amount of the temperature variation is small in comparison with the temperature change induced by the interaction of the analyte 132 with the assay polymer 214. In some embodiments, the heat sink 230 may provide a thermal wave 202 having a frequency from about 0.001 to about 0.5 Hz, such as from about 0.005 to about 0.1 Hz, or from about 0.01 to about 0.05 Hz. Furthermore, the frequency of the thermal wave 202 may vary during testing (e.g., the frequency may be continuously varied from a low frequency to a high frequency or vice versa). The thermal wave 202 may have an amplitude of about 1.0° C. or less, about 0.4° C. or less, or even about 0.10° C. or less.

The temperature of the thermocouple 210 may be tested, and the result may be compared with the temperature of the heat sink 230 (as measured at the thermocouple 232).

The concentration of the analyte 132 in the liquid 124 may be calculated at least in part on a phase shift between the thermal wave 202 produced by the heat sink 230 and the attenuated thermal wave 204 wave at the thermocouple 210. A comparison of the thermal wave 202 and the attenuated thermal wave 204 may be performed by the processor 236 based on responses of liquids of known concentration. In some embodiments, the comparison of the thermal wave 202 with the attenuated thermal wave 204 may be based at least in part on the amplitudes, the phase shift, or another property.

Measurement of the thermal wave enables measurement of thermal resistance without significantly changing the overall temperature of the assay polymer 214. Without being bound to any particular theory, such a measurement appears to be a thermal analog to the measurement of capacitance or inductance in the field of electronics. For example, measuring resistance reveals some information about an electronic device or material, but measuring capacitance or impedance reveals additional information, such as how the device or material responds to a load. Similarly, measuring thermal resistance by the methods disclosed herein can reveal additional information that measuring a steady-state temperature difference cannot.

For example, when applying a thermal wave, different types of information are available in the form of a change in amplitude, frequency and/or phase of the attenuated thermal wave upon binding of a target to the receptor. The phase shift may vary based on the frequency of the input. The amount of information provided by a thermal wave is greater than steady-state analysis, and the information may enable detection or differentiation of a wider variety of materials.

Furthermore, and again without being bound to any particular theory, an increase in thermal mass of the assay polymer 214 may occur upon binding of the analyte 132 onto its receptor (i.e., the cavities therein). Before binding of the analyte 132, the cavities may be filled with liquid. Upon binding of the analyte 132 into its receptor, the liquid may be replaced by the analyte 132, thus increasing the thermal mass of the entire coated thermocouple 210.

EXAMPLES

Example 1: Preparation of MIP Having a Template for Detecting Dopamine

Ethylene glycol dimethacrylate (EGDM), methacrylic acid (MAA), dopamine hydrochloride salt (99%), and methanol were purchased from Acros Organics (Loughborough, United Kingdom). Prior to polymerization, the stabilizers in the MAA and EGDM were removed by filtration over alumina. 4,4'-azobis(4-cyanovaleric acid) and serotonin creatinine sulfate monohydrate (98%) were purchased from Sigma-Aldrich (Gillingham, United Kingdom).

A mixture of MAA (0.54 g, 6.6 mmol), EGDM (2.96 g, 14.9 mmol), and 4,4'-azobis(4-cyanovaleric acid) (65 mg) was dissolved in methanol (3.67 ml) and water (0.57 ml) together with dopamine (0.063 g, 0.33 mmol), the template molecule. This mixture was degassed with $N_2$ and heated to initiate polymerization. To allow full completion of the reaction, the mixture was kept at 65° C. for 12 hours. After polymerization, the bulk polymer was ground and sieved to obtain microparticles having diameters smaller than 10 μm. Dopamine was removed from the MIP powders by continuous extraction with a 50/50 mixture of methanol and water. After 6 hours, the MIP was substantially free of dopamine, as verified by AT-IR spectroscopy with a NICOLET™ 380 FT-IR device from Thermo Scientific (Loughborough, United Kingdom). Subsequently, the MIP powder was dried in an oven for 12 hours at 100° C. A non-imprinted polymer (NIP) was synthesized as a control according to the same method, but without the presence of the dopamine.

Example 2: Testing of MIP for Detecting Dopamine

Figure 5:
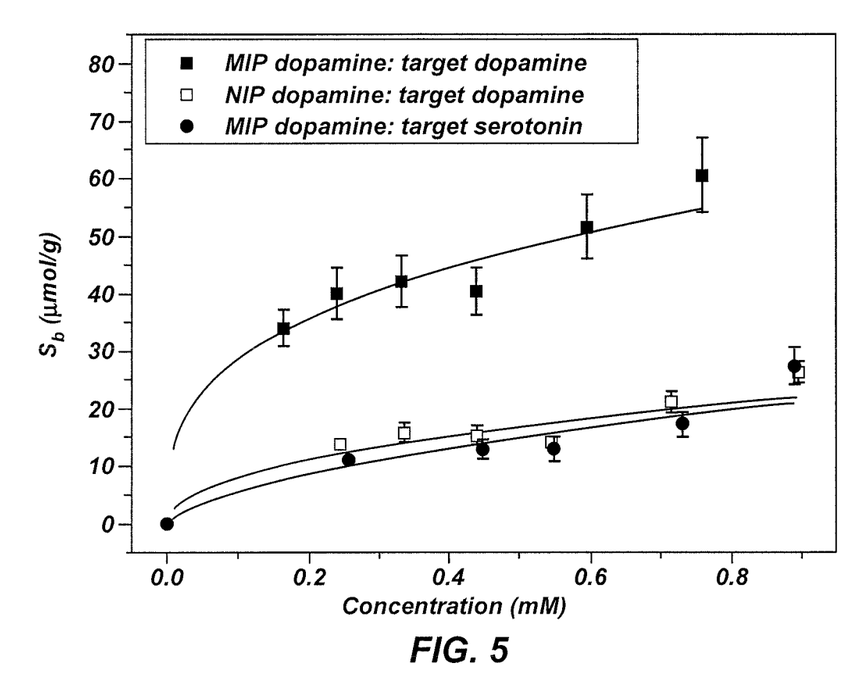
FIG. 5 is a graph showing binding isotherms for dopamine as measured according to an embodiment of the disclosure.

Specificity and binding isotherms of the MIP and NIP particles were determined by optical batch rebinding experiments with an Agilent 8453 UV-visible spectrophotometer (Santa Clara, Calif.). For the rebinding experiments, 20 mg of MIP or NIP powder was added to 5 ml of aqueous dopamine solutions in concentrations between 0.3 to 1.0 mM. The resulting suspensions were shaken for 12 hours on a rocking table at room temperature. Subsequently, the suspensions were filtered and the free concentration of dopamine ($C_f$) was determined by UV-vis spectroscopy. The bound concentrations ($S_b$) of dopamine were calculated per gram of MIP and NIP and binding isotherms, and are shown in FIG. 5. By fitting the binding isotherms, the specificity of the MIP toward the template dopamine was determined. To test the selectivity, the competitor molecule serotonin was used, since its structure is very similar to dopamine. For these experiments, 20 mg of MIP powder was added to 5 ml of aqueous serotonin solutions and binding isotherms were determined after filtration of the suspensions.

FIG. 5 shows that there is a significant difference in binding between the MIP and its reference, the NIP. To determine the specificity, the imprint factor (IF) was used, which is the amount bound to the MIP divided by the amount bound to the reference NIP at a selected concentration. The binding isotherms were fitted with a two-parameter fit of the following type to analyze the imprint factor at a specific concentration (Equation 1):

$$S_b = A \cdot C_f^v \quad \text{Equation 1:}$$

Equation 1 corresponds to the Freundlich isotherm and may be used for fitting of MIP binding isotherms if the distribution of the binding sites and affinity constants are assumed to be heterogeneous. At $C_f=0.3$ mM, the IF was 3.1±0.1, whereas higher concentrations yielded slightly lower IF values (~2.5) due to saturation of the binding sites. The results were comparable to other dopamine MIPs in literature. The response of the MIP to the competitor serotonin was not significantly different than the reference, demonstrating the selectivity of the system.

Example 3: Preparation of MIP-Coated Thermocouples

PLLA was mixed with chloroform at 60° C. under a water reflux for 120 minutes to ensure dissolution of the PLLA and a negligible loss of chloroform. The concentration of the resulting solution was 200 μg/mL.

Mineral-insulated Type K thermocouples having diameters of 0.5 mm and lengths of 30 cm were obtained from TC Direct, of Nederweert, the Netherlands. The thermocouples were dipped into the PLLA-chloroform solution for 10 seconds and withdrawn at the rate of 0.39 cm/min. The chloroform was evaporated to leave a coating of PLLA having a thickness of approximately 0.09 mm (90 μm) on the thermocouples.

The PLLA coated thermocouples were heated to the glass transition temperature of the PLLA polymer, between 65° C. and 75° C. The thermocouples were manually roll coated with the MIP or NIP powder formed in Example 1. Subsequently, the coated thermocouples were placed in a refrigerator at 4° C. for approximately 5 minutes to allow the PLLA polymer to be brought back to its crystalline state. The thermocouples were then washed with isopropanol in order to wash away loosely associated or excessive MIP or NIP particles to leave securely attached MIP or NIP particles.

Example 4: Heat-Transfer Method for Detection of Dopamine with MIP-Coated Thermocouples A 1× phosphate buffered saline (PBS) solution was prepared with Dulbecco tablets obtained from Oxoid Limited (Basingstoke, United Kingdom). MIP-coated and NIP-coated thermocouples were sequentially exposed in a flow cell to fixed concentrations of dopamine in a phosphate-buffered saline (PBS) buffer solution. Solutions of dopamine in concentrations of 0.5 μM, 1 μM, 2 μM, 5 μM, 10 μM, 15 μM, 20 μM, 25 μM, and 50 μM were pumped in ascending succession. At first, the flow cell was flushed with PBS and left for at least 45 minutes to allow temperature stabilization to occur. Afterwards, 3 ml of the lowest concentration (0.5 μM) was added over 12 minutes, at a constant rate of 0.25 ml/min. Before the addition of the next concentration, the flow cell was left to equilibrate for 30 minutes. Thus, a pattern of 12 minutes addition by constant pumping and 30 minutes stabilization was kept throughout each measurement. A copper heating element in the flow cell in contact with the solution was maintained at 37° C. by controlling a voltage across a resistor in thermal contact with the copper heating element. The change in voltage required to maintain the temperature was recorded, and is shown in FIG. 6A.

Figure 6A:
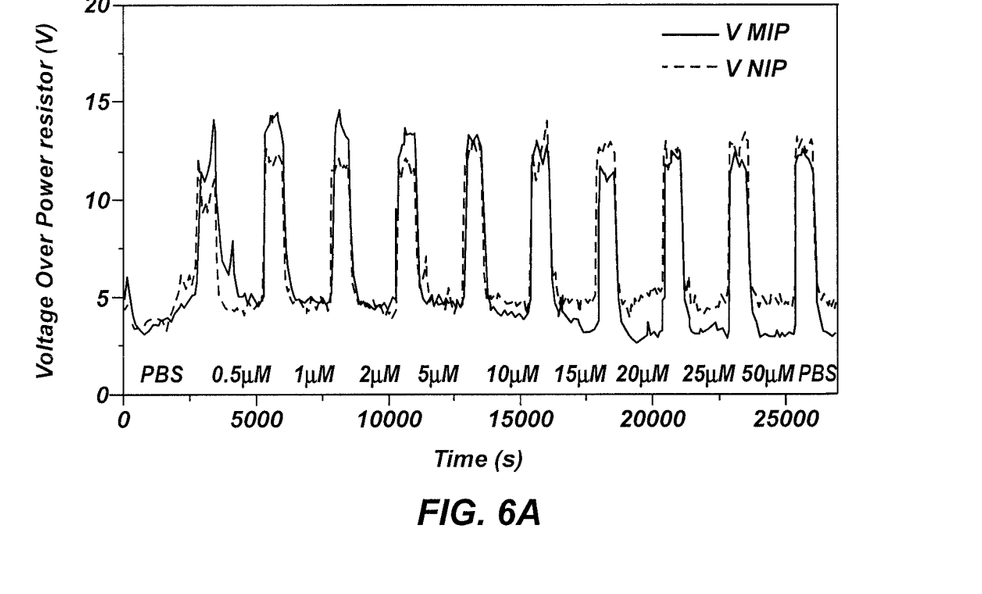
FIG. 6A is a graph showing power requirements for different concentrations of dopamine passing over devices as shown in FIGS. 1 through 3C.
Figure 6B:
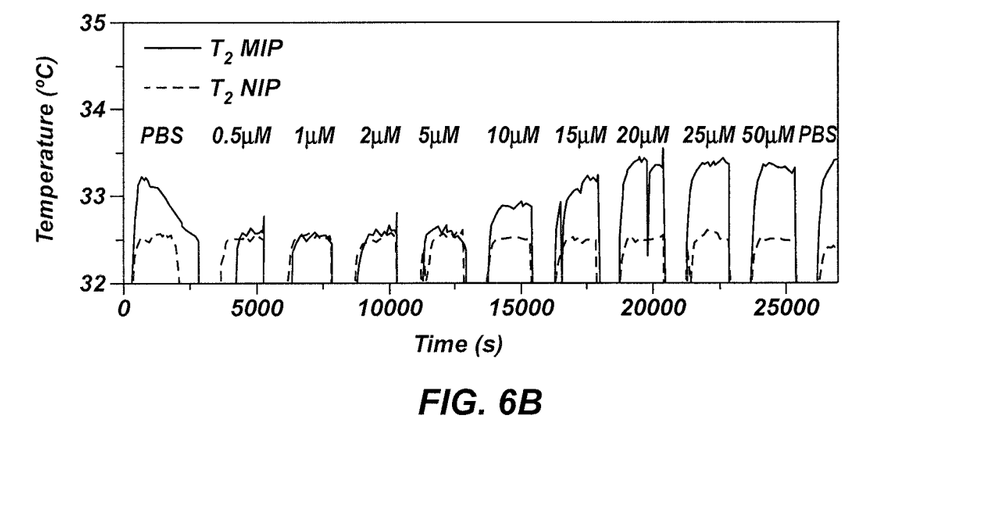
FIG. 6B is a graph showing temperatures for different concentrations of dopamine passing over devices as shown in FIGS. 1 through 3C.

As seen in FIG. 6B, increasing concentrations of dopamine correspond to an increase in temperature of the MIP-coated thermocouple ($T_2$ MIP). Furthermore, the voltage required to maintain the copper element at 37° C. (V MIP) decreases concurrently with increased dopamine concentration. When the copper heating element is maintained at a temperature of 37° C., buffer solution in the flow cell is at a temperature of about 32.5° C., and receptor cites on the MIP coating are unoccupied. Also shown in FIG. 6B, the temperature of the NIP-coated thermocouple ($T_2$ NIP) was maintained constant throughout the experiment. Furthermore, the voltage required to maintain the copper element at 37° C. (V NIP) did not decrease when the concentration of dopamine increased. The MIP experiment was repeated two more times to investigate the reproducibility of the attachment method used, with similar results.

FIGS. 6A and 6B show that there is no significant response by the NIP-coated thermocouple to any dopamine-PBS additions. This indicates that the MIP coating is the source of the temperature variations observed between the MIP-coated thermocouple and the NIP-coated thermocouple.

The temperature for MIP-coated thermocouples ($T_2$ MIP) was constant at about 32.5° C. for the first four additions of dopamine-PBS. Upon addition of 10 μM dopamine, there was a significant increase in $T_2$, which continues for the subsequent higher concentrations. This can be explained by a change in thermal resistance of receptors of the MIP. Heat loss occurs through unoccupied receptors, which appear to be present for the first four dopamine-PBS additions to the MIP-coated thermocouples as well as for all additions to the NIP-coated thermocouples. Upon occupation of the MIPs by dopamine, an insulation layer appears to be created, decreasing heat loss through the thermocouple; hence the overall temperature of the flow cell increases to a maximum of 33.5° C. for concentrations above 20 μM DA. The increase in the temperature measured by the MIP-coated thermocouple may be explained by the retention of heat energy by the insulating layer.

The increase in the temperature measured ($T_2$) is accompanied by a decline in voltage over power resistor (V MIP), meaning that less power is needed to keep the copper element at a constant 37° C., since heat loss from the flow cell has decreased. Meanwhile, V NIP stays constant throughout the experiment. The ambient temperature was found to be stable at room temperature, meaning that a change in $T_2$ could not be attributed to a change in ambient temperature. Thus, the increase in $T_2$ appears to correspond to the occupation of MIPs by dopamine.

Furthermore, because V MIP is associated with a change in $T_2$, the concentration of dopamine in the liquid may be inferred based on a measurement of V MIP alone, $T_2$ alone, of both V MIP and $T_2$ in combination.

Figure 7:
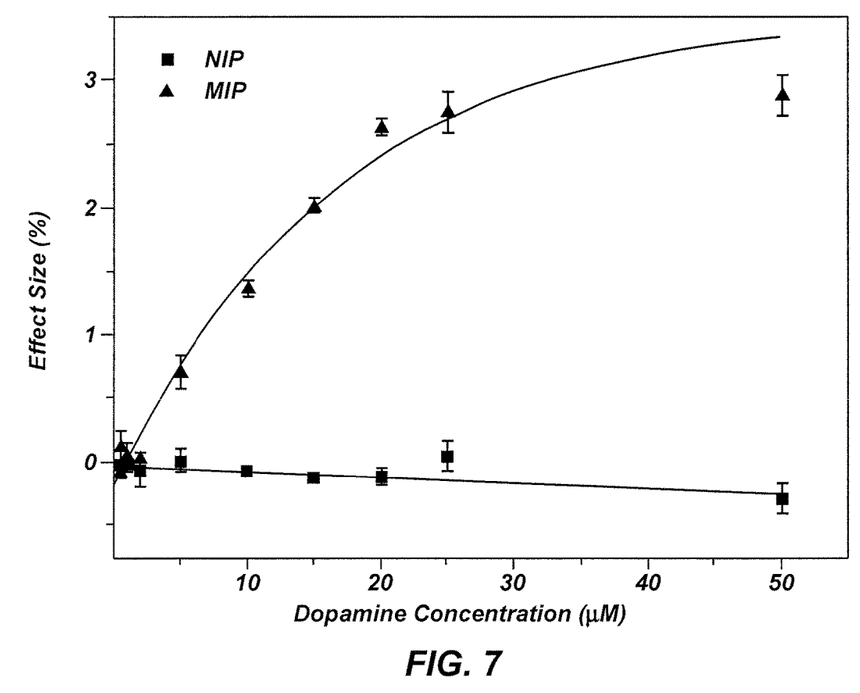
FIG. 7 is a graph showing dose-response curves comparing the response of devices according to an embodiment of the disclosure.

FIG. 7 compares dose-response curves for thermocouples coated with MIPs and NIPs when exposed to various concentrations of dopamine. For MIPs, there is an increase in response with increasing dopamine concentrations. The data suggest that the limit of detection for dopamine by the MIP-coated thermocouples as prepared in Example 3 may be approximately 5 μM dopamine and that MIP saturation may be reached between about 20 μM and 25 μM dopamine. NIP-coated thermocouples did not show any significant response to the increase in dopamine concentrations.

Thermocouples and sensors as described herein may offer benefits as compared to conventional sensors. For example, thermocouples may be relatively easier to prepare, because methods such as dip-coating may be scaled to production quantities while retaining uniform (reproducible) characteristics. Furthermore, though a thermocouple may have a much smaller surface area than a flat substrate, the detection sensitivity of a thermocouple per unit of surface are may be higher than the detection sensitivity of flat substrates. Thus, the thermocouple may be both smaller and more sensitive. Thus, thermocouples and sensors may be used for microfluidics and in vivo testing, applications for which flat substrates may not be practical. Coating of thermocouples may be relatively easier than coating of flat substrates because a smaller volume of liquid may be needed.

While the present disclosure has been described herein with respect to certain illustrated embodiments, those of ordinary skill in the art will recognize and appreciate that it is not so limited. Rather, many additions, deletions, and modifications to the illustrated embodiments may be made without departing from the scope of the disclosure as hereinafter claimed, including legal equivalents thereof. In addition, features from one embodiment may be combined with features of another embodiment while still being encompassed within the scope of the disclosure as contemplated by the inventors. Further, embodiments of the disclosure have utility with different and various detection devices and methods.

What is claimed is:

1. A device for detecting an analyte, the device comprising:
   a thermocouple; and
   an assay polymer on a surface of the thermocouple, the assay polymer formulated to bind to the analyte, wherein a heat transfer property of the assay polymer varies responsive to an amount of the analyte bound thereto.

2. The device of claim 1, further comprising a processor programmed to calculate an amount of the analyte bound to the assay polymer.

3. The device of claim 2, wherein the processor is programmed to calculate a concentration of the analyte in a liquid in contact with assay polymer based at least in part on the amount of the analyte bound to the assay polymer.

4. The device of claim 3, wherein the processor is programmed to detect a phase shift between a thermal wave at a heat transfer element and an attenuated thermal wave at the thermocouple.

5. The device of claim 4, wherein the processor is programmed to calculate the concentration of the analyte in the liquid based at least in part on a difference in amplitude between the thermal wave at the heat transfer element and the attenuated thermal wave at the thermocouple.

6. The device of claim 1, further comprising a base material on the thermocouple, wherein the assay polymer is secured to a surface of the base material.

7. The device of claim 1, wherein the assay polymer comprises a molecularly imprinted polymer.

8. The device of claim 1, wherein the assay polymer comprises a material selected from the group consisting of DNA, RNA, proteins, and portions and analogs thereof.

9. The device of claim 1, wherein the assay polymer is formulated to bind to the analyte in a liquid when the liquid is in contact with the assay polymer.

10. A method of forming a device for detecting an analyte comprising a thermocouple, the method comprising:
    providing an assay polymer on a surface of the thermocouple, the assay polymer formulated to bind to the analyte, wherein the assay polymer is formulated such that a heat transfer property of the assay polymer varies responsive to an amount of the analyte bound to the assay polymer.

11. The method of claim 10, wherein providing an assay polymer comprises providing a molecularly imprinted polymer on the surface of the thermocouple.

12. The method of claim 10, further comprising coating the surface of the thermocouple with a base material and wherein providing an assay polymer on the surface of the thermocouple comprises securing the assay polymer to the base material.

13. The method of claim 12, further comprising heating the base material to a glass transition temperature thereof prior to securing the assay polymer to the base material.

14. The method of claim 13, further comprising cooling the base material below the glass transition temperature to crystallize the base material and retain at least a portion of the assay polymer thereon.

15. The method of claim 13, wherein providing the assay polymer comprises rolling the thermocouple in a powder comprising the assay polymer after the base material has reached the glass transition temperature.

16. The method of claim 14, further comprising washing the thermocouple to remove an unretained portion of the assay polymer from a surface of the base material.

17. A method for detecting an analyte, the method comprising:
passing a liquid containing an analyte adjacent to and in contact with a thermocouple having an assay polymer on a surface of the thermocouple, the assay polymer formulated to bind to the analyte, wherein a heat transfer property of the assay polymer varies responsive to an amount of the analyte bound to the assay polymer;
binding the analyte to the assay polymer;
detecting a temperature of the thermocouple; and
calculating a concentration of the analyte in the liquid based at least in part on the heat transfer property of the assay polymer.

18. The method of claim 17, further comprising providing a thermal wave comprising a change in a temperature of the liquid.

19. The method of claim 18, wherein calculating a concentration of the analyte in the liquid comprises determining a difference in amplitude between the thermal wave at an interface between the liquid and the assay polymer and an attenuated thermal wave at the thermocouple.

20. The method of claim 17, wherein calculating a concentration of the analyte in the liquid comprises calculating a concentration of a biological analyte in the liquid.

\* \* \* \* \*